United States Patent
Walsh et al.

(10) Patent No.: US 7,534,450 B2
(45) Date of Patent: *May 19, 2009

(54) NUTRIENT SUPPLEMENTS AND METHODS FOR TREATING AUTISM AND FOR PREVENTING THE ONSET OF AUTISM

(75) Inventors: William John Walsh, Naperville, IL (US); Anjum Iona Usman, Lisle, IL (US)

(73) Assignee: The Health Research Institute, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/803,083

(22) Filed: May 11, 2007

(65) Prior Publication Data
US 2007/0224290 A1 Sep. 27, 2007

Related U.S. Application Data

(62) Division of application No. 11/526,383, filed on Sep. 25, 2006, now Pat. No. 7,232,575, which is a division of application No. 09/998,342, filed on Nov. 30, 2001, now abandoned.

(60) Provisional application No. 60/250,404, filed on Nov. 30, 2000.

(51) Int. Cl.
A61K 47/00 (2006.01)
A23L 1/30 (2006.01)
(52) U.S. Cl. .............................. 424/439; 426/72; 426/73
(58) Field of Classification Search ...................... None
See application file for complete search history.

(56) References Cited

U.S. PATENT DOCUMENTS

| 5,556,644 | A |  | 9/1996 | Chandra ...................... 424/630 |
| 5,976,579 | A |  | 11/1999 | McLean ...................... 424/692 |
| 6,132,724 | A |  | 10/2000 | Blum ...................... 424/195.1 |
| 6,143,332 | A |  | 11/2000 | McLean ...................... 424/692 |
| 6,228,875 | B1 | * | 5/2001 | Tsai et al. .................... 514/380 |
| 6,245,360 | B1 |  | 6/2001 | Markowitz .................. 424/641 |
| 6,399,114 | B2 |  | 6/2002 | Foreman |
| 7,232,575 | B2 | * | 6/2007 | Walsh et al. ................. 424/439 |
| 2001/0055645 | A1 |  | 12/2001 | Flook et al. |

FOREIGN PATENT DOCUMENTS

| EP | 0 891 719 A1 | 1/1999 |
| WO | WO 91/11117 | 8/1991 |
| WO | WO 98/41113 | 9/1998 |
| WO | WO 00/67576 | 11/2000 |
| WO | WO 01/26642 A2 | 4/2001 |

OTHER PUBLICATIONS

Walsh et al., "Eleveated Blood Cooper/Zinc Ratios in Assaultive Young Males," Physiology & Behavior, vol. 62, No. 2, 1997.

Isaacson et al., "Autism: A Retrospective Outcome Study of Nutrient Therapy," Journal of Applied Nutrition, vol. 48, No. 4, 1996.

Kirkman Laboratories, Inc., Kirkman's HypoAllergenic NuThera® Capsules [http://www.kirkmanlabs.com/products/articles/nutherap5p.htm] 1-3 (Mar. 2002).

Kirkman Laboratories, Inc., "Super NuThera®" [http://www.kirkmanlabs.com/products/articles/supernuthera.htm] 1-19 (Mar. 11, 2002).

Kirkman Laboratories, Inc., "Super Nu-Thera with P5P" [http://www.kirkmanlabs.com/products/articles/supernutherap5p.htm] 1-3 (Mar. 11, 2002).

Maret, "The Function of Zinc Metallothionein: A Link between Cellular Zinc and Redox State", J. Nutr. 130( No. 5, Suppl.): 1455S-1458S (May 2000).

Sullivan et al., "Metallothionein Expression Is Increased in Monocytes and Erythrocytes of Young Men during Zinc Supplementation", J. Nutr. 128:7077-713 (1998).

Suzuki et al, "Table I. Factors that induce thionein synthesis in cultured cells in vivo", In, Metallothionein III; Biological Roles & Medical Implications, Birkhauser Verlag, un-numbered page (1993).

Walsh et al., "Disordered Metal Metabolism in a Large Autism Population", Abstract NR823, American Psychiatric Association Annual Meeting, New Orleans, LA (May 10, 2001).

Walsh et al. "Elevated Blood Copper/Zinc Ratios in Assaultive Young Males" Physiology & Behavior, 62(2):327-329 (1997).

Walsh et al., "Metallothionein and Autism", Pfeiffer Treatment Center, 1804 Centre Point Drive, Naperville, Illinois, 60563 (Oct. 2001).

Walsh et al. "Metallothionein Protein Dysfunction in Autism spectrum Disorders", Abstract for International Meeting For Autism Research, San Diego, CA (Nov. 9-10, 2002).

Autism Research Publication, "Parent Ratings of Behavioral Effects of Drugs,. Nutrients, and Diets," ART Publ. 34, Autism Research Institute, 4182 Adams Avenue, San Diego, CA 921 16 (Sep. 2000).

(Continued)

Primary Examiner—S. Tran
(74) Attorney, Agent, or Firm—Merchant & Gould PC

(57) ABSTRACT

Provided by the present invention are novel and non-obvious nutrient supplements that preferably comprise minerals, vitamins, amino acids, and agents capable of delivering cysteine in vivo. The nutrient supplements desirably are capable of promoting metallothioneins, and optionally, promoting the removal of excess metals from the bloodstream. Also provided by the invention are methods of treating autism involving administration of the nutrient supplements. The methods include treatment to prevent or slow down the onset of autism once a predisposition for the development of autism has been detected, and treatment to alleviate or reverse the symptoms of autism once autism has been diagnosed. The invention further provides methods of administering the nutrient supplements in the treatment of other diseases, disorders and conditions, that would benefit from such administration, especially those that would benefit from metallothionein promotion and/or removal of excess metals from the bloodstream.

11 Claims, No Drawings

OTHER PUBLICATIONS

Fischer et al., "Commentary: Recent excitement regarding metallothionein", *Proc Natl. Acad. Sci. USA*, 95:3333-3334 (Mar. 1998).

Isaacson et al., "Autism: A Retrospective Outcome Study of Nutrient Therapy ," *Journal of Applied Nutrition*, 48(4):2-6 (1996).

Jacob et al., "Control of zinc gransfer between thionein, metallothionein, and zinc proteins," Proc. *Natl Acad Sci. USA*, 95:3489-3494 (Mar. 1998).

Jiang et al., "The Glutathione redox couple modulates zinc transfer from metallothionein to zinc-depleted sorbitol dehydrogenate," *Proc. Natl Acad. Sci. USA*, 94 :3483-3488 (Mar. 1998).

Karen, from the autismandenzymes Yahoo.Group, William Walsh - PfeifferJMetallathionein* [http: //www . bbbautism.com/dan~william_walsh. html] 1-9.

Kirkman Laboratories, INc., "Kirkman's Amino-Support" 1 [http: // www . kirkmanlabs.com/products/articles/aminosupport.htm] 1-5 (Mar. 11, 2000).

Cutler, "Pyridoxine and Trace Element Therapy in Selected Clinical Cases." Orthomolecular *Psychiatry*, vol. 3, No. 2, pp. 89-95 (1 974).

Isaacson et al., "A Retrospective Outcome Study of Nutrient Therapy." Journal *of Applied* Nutrition, vol. 48. No. 4, pp. 110-118 (1 996).

* cited by examiner

NUTRIENT SUPPLEMENTS AND METHODS FOR TREATING AUTISM AND FOR PREVENTING THE ONSET OF AUTISM

RELATED APPLICATIONS

This application claims the benefit of U.S. Provisional Application Ser. No. 60/250,404, filed Nov. 30, 2000, which is fully incorporated herein by reference.

TECHNICAL FIELD OF THE INVENTION

The present invention pertains to novel and non-obvious nutrient supplements. Preferably the supplements comprise minerals, vitamins, amino acids, and agents capable of delivering cysteine in vivo. The nutrient supplements desirably are capable of promoting metallothioneins, and optionally, promoting the removal of excess metals from the bloodstream. The invention also pertains to methods of treating autism involving administration of the nutrient supplements. The methods include treatment to prevent or slow down the onset of autism once a predisposition for the development of autism has been detected, and treatment to alleviate or reverse the symptoms of autism once autism has been diagnosed. The nutrient supplements also optionally can be employed in the treatment of other diseases, disorders and conditions, as described herein, particularly those that would benefit from metallothionein promotion and/or removal of excess metals from the bloodstream.

BACKGROUND OF THE INVENTION

Autism is a developmental disorder that affects brain function, interfering with reasoning ability, imagination, communication, and social interaction. Formerly a rare disorder, autism has increased in the last decade by 300% to 500% in the United States and many other countries. Clearly, a means of prevention and treatment of what is now an epidemic are needed. A variety of different types of autism treatments premised on a variety of different theories regarding the development of autism (e.g., that it is due to a persistent atypical viral infection in patients administered live attenuated combination vaccinations, that it results from toxic metals such as mercury in the context of autoimmunity, that it results from affecting retinoid receptors in the brain through disruption of the G-alpha protein, and other theories) presently exist. However, what is needed is an approach to autism that addresses the underlying causes of autism, as opposed to one that merely treats or even masks the symptoms.

An approach that treats the symptoms and potentially the causes of autism is the individualized nutrient therapy for autism, such as reported in Isaacson et al., *Journal of Applied Nutrition*, 48, 110-118 (1996), the Autism Research Publication "Patient Ratings of Behavioral Effects of Drugs, Nutrients, and Diets", ARI Publ. 34, Autism Research Institute, 4182 Adams Avenue, San Diego, Calif. 92116, September 2000, as well as in other references. This individualized therapy relies on treatment optimized for the individual's particular chemical imbalance, with particular nutrients emphasized in certain imbalances, and others avoided.

Recently, methods of testing for a predisposition to autism, for preventing or delaying the onset of autism once a predisposition for autism has been detected, and for treating the symptoms of autism once autism has developed, have been described based on the surprising discovery of an inborn error of metal metabolism underlying the etiology of autism, which is signaled, among other things, by substantially elevated Cu/Zn levels in blood. (See, Walsh et al., "Disordered Metal Metabolism in a Large Autism Population", Abstract NR823, American Psychiatric Association Annual Meeting, New Orleans, La., May 10, 2001, and "Metallothionein and Autism", October 2001, publication of the Pfeiffer Treatment Center, Naperville, Ill. (each incorporated by reference in their entireties)). This suggests that effective autism prevention and/or treatment can be achieved by (1) early infant screening for disordered metal metabolism followed by treatment of any disorder uncovered, and (2) vigilant avoidance of toxic metals for at-risk children (e.g., children identified as having a predisposition for the development of autism).

Furthermore, these findings suggest that a disorder of the function of metallothioneins (MTs) underlies autism. Metallothioneins are short, linear, cysteine-rich proteins composed of between sixty-one and sixty-eight amino acids. They have been highly conserved over time and throughout a wide array of species, suggesting that they are essential for life. All human MTs contain twenty cysteine residues and have an "s" configuration with extraordinary metal-binding capability. MTs bind with zinc, lead, copper, mercury, silver, and cadmium both in the intestinal tract and in the liver. In terms of the relativity affinity of metals for metallothionein, mercury exhibits the highest affinity for MTs, and copper, cadmium, lead, and zinc exhibit successively lower affinities for MTs. Functions of MTs include (1) limitation of the amounts of Hg, Pb, and other toxic metals which can be absorbed by the body, and (2) sequestering of toxic metals in "safe" MT molecules of fairly high stability.

The consequences of insufficient metallothionein activity (i.e., also described herein as "MT dysfunction") include, but are not limited to, the following:

(1) reduced ability to prevent absorption of Cu, Hg, Pb, and Cd into the portal bloodstream;

(2) dramatically increased toxicity of Hg, Pb, and Cd and other heavy metals in cells and membranes;

(3) impaired homeostasis of Cu and Zn resulting in Cu overload and Zn depletion in brain and periphery;

(4) impaired neuronal development which could result in incomplete maturation of the gastrointestinal tract and brain;

(5) impaired immune function;

(6) dopamine depletion and norepinephrine overload; and (7) occupation of enzyme sulfhydryl groups by Hg and other heavy metals.

However, in particular, metallothionein inactivity (and accordingly, MT dysfunction) greatly increases sensitivity to toxic heavy metals.

Accordingly, the present invention provides novel and non-obvious nutrient supplements that, among other things, are effective for promoting metallothioneins in a person. The invention also provides an effective generic treatment for autism involving administration of the nutrient supplements, which preferably can be employed to treat autism once diagnosed, or to prevent or delay the onset of autism in persons predisposed to the development of autism. Moreover, the invention provides generic treatment involving administration of nutrient supplements that optionally can be employed in the treatment of other diseases, disorders, or conditions that would benefit from promotion of metallothioneins. These and other objects and advantages of the present invention, as well as additional inventive features, will be apparent from the following description of the invention provided herein.

BRIEF SUMMARY OF THE INVENTION

The present invention provides novel and non-obvious nutrient supplements that preferably comprise minerals, vitamins, amino acids, and agents capable of delivering cysteine in vivo. The nutrient supplements preferably are capable of promoting metallothioneins, and optionally, promoting the removal of excess metals from the bloodstream. The invention also provides methods of treating autism involving administration of the nutrient supplements that preferably include treatment to prevent or slow down the onset of autism once a predisposition for the development of autism has been detected, and treatment to alleviate or reverse the symptoms of autism once autism has been diagnosed. The nutrient supplements of the invention also optionally can be employed in the treatment of other diseases, disorders and conditions as described herein, especially those that would benefit from promotion of metallothioneins and/or removal of excess metals from the bloodstream.

DETAILED DESCRIPTION OF THE INVENTION

The present invention provides nutrient supplements that preferably comprise minerals, vitamins, amino acids, and agents capable of delivering cysteine in vivo, and which desirably are capable of promoting metallothioneins in a person, In particular, the nutrient supplements preferably comprise: (1) minerals capable of promoting metallothioneins (e.g., minerals zinc and selenium); (2) vitamins capable of promoting metallothioneins (e.g., vitamins B6, A, C, and E, and the coenzyme form of vitamin B6, pyridoxal-5'-phosphate); (3) nonessential amino acids effective for removal of excess metals from the bloodstream (e.g., taurine); and (4) agents capable of delivering cysteine in vivo (e.g., the tripeptide glutathione). The nutrient supplements further optionally comprise a mixture of amino acids effective for promoting metallothioneins in a person, e.g., especially the amino acids serine, lysine, alanine, glycine, threonine, proline, aspartic acid, asparagine, glutamic acid, methionine, glutamine, isoleucine, and valine, and optionally the amino acid cysteine.

Among other things, the nutrient supplements can be employed in methods for preventing or delaying the onset of autism in a person, in reducing the symptoms of autism in a person, and in the treatment of other diseases, disorders and conditions as described herein, e.g., those that would benefit from promotion of metallothioneins and/or removal of excess metals from the bloodstream. The methods preferably comprise first treating the person with a treatment regimen comprising detoxification of patients by removal of excess heavy metals, and optimally, by administration of zinc and other components of the nutrient supplements. The methods next preferably comprise administering the nutrient supplements to better balance and even potentially achieve normal metal metabolism, ostensibly by promoting metallothioneins. Such treatments desirably are sufficient to prevent or delay the onset of autism in the person, or to reduce the symptoms of autism or other diseases, disorders, and conditions being treated.

Certain standard terms are employed in describing the invention. Illustrative definitions of these terms are set out as follows. Should there be any term that is left undefined, or any possible ambiguity in the meaning of a term, the broadest possible definition known in the medical and scientific fields that is consistent with the scope and goals of the invention is intended to be applied.

Nutrient Supplements According to the Invention

The prior art teaches that nutrient therapy, as applied on an individual basis, "is quite effective in ameliorating the symptoms of autism and related disorders" (Isaacson et al., *Journal of Applied Nutrition*, 48, 110-118 (1996)). By contrast, the present invention provides nutrient supplement formulations, i.e., Metallothionein Promotion ("MTP") Supplements (as well as component thereof) that can be employed generically in the treatment or prevention of autism, as well as potentially in the treatment of other diseases, disorders, and conditions. Without being bound by any theory, the MTP Supplements are predicated on the provision of ingredients that promote (e.g., boost or increase) the amounts and/or functioning of one or more metallothionein(s), and which is referred to herein merely as "promoting metallothioneins" or "metallothionein promotion". As described herein, metallothioneins appear to play a role in a variety of diseases, disorders and conditions, most notably in autism, such that the MTP Supplement optionally can be employed in the treatment of diseases, disorders, and conditions that would benefit from such promotion of metallothioneins. The ability of the nutrient supplements to promote metallothioneins is provided by the particular minerals, vitamins, amino acids, and agents capable of providing cysteine that are present in the MTP Supplement. However, other analogous (i.e., equivalent) components can be employed in the MTP Supplements. The MTP Supplements further preferably have the ability to promote (i.e., to facilitate, assist, or cause) the removal of excess metals from the bloodstream.

In particular, the nutrient supplements (i.e., the MTP Supplements) preferably comprise: (1) minerals capable of promoting metallothioneins (e.g., zinc and selenium); (2) vitamins capable of promoting metallothioneins (e.g., vitamins B6, A, C, and E, and the coenzyme form of vitamin B6, pyridoxal-5'-phosphate); (3) nonessential amino acids effective for removal of excess metals from the bloodstream (e.g., taurine); and (4) agents capable of delivering cysteine in vivo (e.g., the tripeptide glutathione). Many of these components have additional functions apart from promoting metallothioneins that are useful or advantageous in the nutrient supplements of the invention. Namely, selenium also has been shown to result in risk reduction for at least some types of cancer. Vitamins C and E are capable of acting as free radical scavengers. Vitamin B6 and the coenzyme form of vitamin B6, pyridoxal-5'-phosphate, are capable of augmenting the utilization of zinc—with pyridoxal-5'-phosphate being better absorbed by persons with malabsorption. Glutathione also is capable of assisting in the detoxification of heavy metals.

The nutrient supplements further optionally comprise a mixture of amino acids (i.e., amino acids other than and in addition to the non-essential amino acid taurine that optimally is present in the supplement) effective for the promotion of metallothioneins in a person. Preferably this mixture comprises the amino acids serine, lysine, alanine, glycine, threonine, proline, aspartic acid, asparagine, glutamic acid, methionine, glutamine, isoleucine, and valine, as well as, optionally, the amino acid cysteine.

The MTP Supplement optionally can be employed in the generic treatment for the metallothionein dysfunction present in nearly all autistic persons and all persons predisposed to autism, and in the generic treatment of persons having other diseases, disorders, or conditions that impact metallothionein function and which would benefit from promotion of metallothioneins and/or promotion of removal of excess metals from the bloodstream. Additional, or altered, nutrients can be employed for autistic persons having anemia, methylation disorders, fatty-acid imbalances, malabsorption, and the like. In particular, the present invention provides MTP Supplements in the form of a so-called "Basic MTP Supplement", as well as a "Modified MTP Supplement" that is appropriate for patients with sensitive gastrointestinal tracts. The Modified MTP Supplement differs from the Basic MTP Supplement in that in the modified formulation the cysteine is provided not as cysteine, but rather in the form of additional glutathione. Glutathione breaks down in the intestines to cysteine and other amino acids.

Preferably the MTP Supplements, i.e., the Basic MTP Supplement and the Modified MTP Supplement, each comprise the ingredients which follow. These nutrient supplements were designed and are described herein based on what appears to be the optimal levels of nutrients appropriate for dosing a small child (e.g., 25 to 50 lbs). Larger persons generally require larger doses, depending on body weight. Accordingly, the MTP Supplements (i.e., the Basic MTP Supplement or the Modified MTP Supplement) are defined in terms of one "unit dose" of the formula. For a smaller individual, typically one unit dose/per day is preferred for administration (i.e., once optimal levels of nutrients have been achieved, as described herein). For a larger individual, typically more than one unit/dose per day is preferred for administration. Recommended (i.e., preferred) unit dosages are described as a function of a person's weight in Table 1.

TABLE 1

Recommended Unit Dosages As a Function of Patient Weight

| Patient Weight, lbs | Dosage/Day |
| --- | --- |
| 25-50 | 1 unit |
| 51-75 | 2 units |
| 76-125 | 3 units |
| >125 | 4 units |

However, these recommended dosages should be applied only as tolerated by the particular individual. For instance, many autistics may discover that the optimum dosage is less than 1 unit dose/day of the MTP Supplement (e.g., preferring instead from about 0.25 to about 0.5 of the recommended dose). On the other hand other persons being treated with the MTP Supplement may require more per a given weight than the unit dosages set forth in Table 1 (e.g., preferring instead up to about twice the recommended dose). Thus while the daily dosages in Table 1 are the preferred dosages, for a particular person of a given weight, the daily dose optionally can be varied as necessary or desired, e.g., to provide for from about 0.25 of the recommended dose up to about twice the recommended dose for each weight range.

The formulation for the Basic MTP Supplement (component amounts per one unit dose) is set out in Table 2 (and Table 4), and the Modified MTP Supplement (component amounts per one unit dose) is as set out in Table 5 (and Table 6).

TABLE 2

MTP Formulation (i.e., Basic MTP Supplement) - Component Amounts per One Unit Dose

| Component | Range (per unit dose) | Optimal Amount (per unit dose) |
| --- | --- | --- |
| Zinc | from about 50 to about 150 mg | about 75 mg |
| Vitamin B6 | from about 150 to about 750 mg | about 250 mg |
| Pyridoxal-5'-Phosphate | from about 25 to about 125 mg | about 35 mg |
| Ascorbic Acid | from about 500 to about 1000 mg | about 750 mg |
| Vitamin E | from about 200 to about 400 I.U. | about 350 I.U. |
| Selenium | from about 5 to about 25 micrograms | about 10 microgram |
| Glutathione | from about 100 to about 200 mg | about 150 mg |
| Taurine | from about 50 to about 150 mg | about 100 mg |

TABLE 2-continued

MTP Formulation (i.e., Basic MTP Supplement) - Component Amounts per One Unit Dose

| Component | Range (per unit dose) | Optimal Amount (per unit dose) |
| --- | --- | --- |
| Vitamin A | from about 1,500 to about 3,500 I.U. | about 2,500 I.U. |
| Mixture of Amino Acids (preferred component amino acids as in Table 4) | from about 150 to about 250 mg for total weight of mixture | Total weight of mixture of about 200 mg |

Table 2 describes that the Basic MTP Supplement also preferably contains a mixture of amino acids (i.e., a mixture of amino acids capable of promoting metallothioneins). Desirably these additional amino acids are present in the nutrient supplements in an amount and combination so as to provide optimal levels of amino acids for the production/functioning of metallothioneins (MTs) in a person. One way to accomplish such optimization is to provide the amino acids in amounts which ensure that there is an ample supply of particular amino acids needed for incorporation into metallothionein proteins. This can be done, for instance, by supplying the amino acids in the amount ratios in which such amino acids typically are present in metallothionein proteins. MT-I and MT-II are present in all cells in the body, and are the most abundant metallothioneins in the body due to the broad range of their distribution (i.e., by comparison, MT-III is a neuronal growth-inhibitory factor found primarily in the brain, and MT-IV is found primarily in epithelia of skin and upper gastrointestinal tract). The amino acid composition of human MT-I and MT-II is presented in Table 3.

TABLE 3

Amino Acid Composition of Human Metallothioneins MT-I and MT-II

| Amino Acid | Metallothionein I | Metallothionein II |
| --- | --- | --- |
| Cysteine | 20 | 20 |
| Serine | 9 | 8 |
| Lysine | 8 | 8 |
| Alanine | 5 | 7 |
| Glycine | 5 | 5 |
| Threonine | 3 | 2 |
| Proline | 2 | 2 |
| Aspartic Acid | 1 | 3 |
| Asparagine | 2 | 1 |
| Glutamic Acid | 2 | 1 |
| Methionine | 2 | 1 |
| Glutamine | 1 | 1 |
| Isoleucine | 1 | 1 |
| Valine | 0 | 1 |
| TOTAL | 61 | 61 |

As can be seen from this Table, the amino acids optimal for the production of these metallothioneins in a person are cysteine, serine, lysine, alanine, glycine, threonine, proline, aspartic acid, asparagine, glutamic acid, methionine, glutamine, isoleucine, and valine. Based on this information, the optimal amounts of component amino acids for metallothionein promotion which are present in the amino acid mixture of the Basic MTP Supplement (i.e., as described in Table 2) are set out in Table 4.

TABLE 4

Amino Acid Component of MTP Supplement (i.e., Basic MTP Formulation) - Component Amounts

| Amino Acid | Milligrams (Range per One Unit Dose) | Milligrams (Optimal Amount per One Unit dose) | Optimal Weight percent (per about 200 mg total amino acids) |
|---|---|---|---|
| Cysteine | from about 37.5 to about 62.5 | about 50.0 | about 25.0 |
| Serine | from about 20.5 to about 34.4 | about 27.4 | about 13.7 |
| Lysine | from about 26.8 to about 44.6 | about 35.7 | about 17.85 |
| Alanine | from about 12.6 to about 21.0 | about 16.8 | about 8.4 |
| Glycine | from about 8.70 to about 14.5 | about 11.6 | about 5.8 |
| Threonine | from about 6.45 to about 10.8 | about 8.6 | about 4.3 |
| Proline | from about 5.25 to about 8.75 | about 7.0 | about 3.5 |
| Aspartic Acid | from about 6.38 to about 10.6 | about 8.5 | about 4.25 |
| Asparagine | from about 4.13 to about 6.88 | about 5.5 | about 2.75 |
| Glutamic Acid | from about 9.00 to about 15.0 | about 12.0 | about 6.0 |
| Methionine | from about 4.73 to about 7.88 | about 6.3 | about 3.15 |
| Glutamine | from about 3.30 to about 5.50 | about 4.4 | about 2.2 |
| Isoleucine | from about 3.00 to about 5.00 | about 4.0 | about 2.0 |
| Valine | from about 1.65 to about 2.75 | about 2.2 | about 1.10 |

As previously described, the Basic MTP Supplement was modified to produce a Modified MTP Supplement that preferably can be employed for persons with sensitive digestive tracts. The Modified MTP Supplement differs from the Basic MTP Formulation in that the amount of glutathione is increased, and the total amount of amino acids is reduced, due to the absence in the amino acid mixture of any cysteine. One unit dose of the Modified MTP Supplement preferably comprises the component amounts set out in Table 5 (and Table 6).

TABLE 5

Modified MTP Supplement (i.e., Modified MTP Formulation) - Component Amounts per One Unit Dose

| Component | Range (per unit dose) | Optimal Amount (per unit dose) |
|---|---|---|
| Zinc | from about 50 to about 150 mg | about 75 mg |
| Vitamin B6 | from about 150 to about 750 mg | about 250 mg |
| Pyridoxal-5'-Phosphate | from about 25 to about 125 mg | about 35 mg |
| Ascorbic Acid | from about 500 to about 1000 mg | about 750 mg |
| Vitamin E | from about 200 to about 400 I.U. | about 350 I.U. |
| Selenium | from about 5 to about 25 micrograms | about 10 microgram |
| Glutathione | from about 175 to about 350 mg | about 275 mg |
| Taurine | from about 50 to about 150 mg | about 100 mg |
| Vitamin A | from about 1,500 to about 3,500 I.U. | about 2,500 I.U. |
| Mixture of Amino Acids (preferred component amino acids as in Table 6) | from about 100 to about 200 mg for total weight of mixture | Total weight of mixture of about 150 mg |

As with the Basic MTP Supplement, the Modified MTP Supplement preferably comprises a mixture of amino acids which promote metallothioneins in a person, preferably as described in Table 6.

TABLE 6

Amino Acid Component of Modified MTP Supplement - Component Amounts per One Unit Dose

| Amino Acid | Milligrams (Range per One Unit Dose) | Milligrams (Optimal Amount per One Unit dose) | Optimal Weight percent (per about 150 mg Total amino acids) |
|---|---|---|---|
| Serine | from about 20.5 to about 34.4 | about 27.4 | about 13.7 |
| Lysine | from about 26.8 to about 44.6 | about 35.7 | about 17.85 |
| Alanine | from about 12.6 to about 21.0 | about 16.8 | about 8.4 |
| Glycine | from about 8.70 to about 14.5 | about 11.6 | about 5.8 |
| Threonine | from about 6.45 to about 10.8 | about 8.6 | about 4.3 |
| Proline | from about 5.25 to about 8.75 | about 7.0 | about 3.5 |
| Aspartic Acid | from about 6.38 to about 10.6 | about 8.5 | about 4.25 |
| Asparagine | from about 4.13 to about 6.88 | about 5.5 | about 2.75 |
| Glutamic Acid | from about 9.00 to about 15.0 | about 12.0 | about 6.0 |
| Methionine | from about 4.73 to about 7.88 | about 6.3 | about 3.15 |
| Glutamine | from about 3.30 to about 5.50 | about 4.4 | about 2.2 |
| Isoleucine | from about 3.00 to about 5.00 | about 4.0 | about 2.0 |
| Valine | from about 1.65 to about 2.75 | about 2.2 | about 1.10 |

Alternately, the mixture of amino acids which promote metallothioneins in a person (e.g., in either the Basic MTP Supplement or the Modified MTP Supplement) can be provided based on supplying a person with amino acids in ratios optimal for production/functioning of metallothionein I (i.e., as opposed to metallothionein II), optimal for production/functioning of metallothionein II (i.e., as opposed to metallothionein I), or optimal for production/functioning of any other of the metallothioneins present in a person. Similarly, the mixture of amino acids which promote metallothioneins in a person can be provided based on the ratios at which the various metallothioneins are present or active in a person (e.g., if one metallothionein is present or active at 90%, and another at 10%, then provision of the various amino acids in the amino acid mixture can reflect this fact). The skilled artisan is aware of other means to optimize for the promotion of metallothioneins in general, or for promotion of a specific metallothionein or metallothionein activity.

According to the invention, the nutrient MTP Supplements employed in the methods of treatment preferably are either in solid or liquid form. In solid form (e.g., powder form), preferably the nutrient supplements are reconstituted in water or other liquid to form a liquid nutrient supplement. Alternately preferably the solid nutrient supplements are prepared in the form of a pill, tablet, lozenge, or capsule to provide for easy ingestion. For young persons taking the supplements, preferably the nutrient supplements are liquid formulations; older persons may be able to take the nutrients as capsules.

The term "liquid formulation" or "liquid nutrient supplement" employed herein refers to, unless otherwise indicated, a liquid solution or suspension that preferably is flowable at about 25° C., with minimal settlement of solids. A "suspension" as described herein is a two-phase system in which one phase (the dispersed phase, also called the discontinuous or internal phase) is distributed as particles or droplets in a second phase (also called the external phase, continuous phase, or dispersing medium). Suspensions can be made up of particles that are gaseous, liquid, or solid, comprising suspensions which are solid/gas (e.g., aerosol), solid/solid, solid/liquid, liquid/liquid (e.g., emulsions), and gas/liquid (e.g., foams). Preferably the liquid nutrient supplement according to the invention is a liquid/liquid suspension or solution, or a liquid/solid suspension or solution. Preferably such a composition is palatable.

Preferably according to the invention, the nutrient supplement can contain other optional components, e.g., flavors or sweeteners to improve palatability, and/or preservatives to improve shelf life, as described further below.

Constituent Components of the Nutrient Supplements

As used herein, the term "comprising" means various components can be conjointly employed in the MTP Supplements of the invention. Accordingly, the terms "consisting essentially of" and "consisting of" are embodied in the term "comprising". In these supplements, the constituent components optionally can be obtained from any possible source, e.g., commercial vendor, in which they are supplied in a form appropriate for human consumption. Preferably all the nutrients employed are soy-free, corn-free, dairy-free, gluten-free, sugar-free, yeast-free, dye-free, copper-free, and/or toxic metal-free. Instead of being mixed in one ingestible liquid, powder, chewable tablet, tablet, or capsule, preferably the nutrients can be combined in one or more ingestible liquid, powder, chewable tablet, tablet, or capsule, as necessary or desired.

Preferably the nutrient supplements of the invention comprise the mineral zinc. Preferably zinc is applied in one unit dose of the supplement in an amount of from about 50 to about 150 mg, particularly about 65, 70, 75, or 80 mg, especially about 75 mg. Optionally, calcium and/or magnesium also can be applied in the supplement. The minerals preferably are employed in the compositions in the form of any of its well known salts including carbonate, oxide, hydroxide, chloride, sulfate, phosphate, gluconate, picolinate, lactate, acetate, fumarate, citrate, malate, amino acids and the like. However, the particular salt and the level will depend on their interaction with other supplement ingredients. Preferred zinc salts for use in the invention are zinc acetate, zinc citrate, zinc gluconate, or zinc picolinate.

Preferably the nutrient supplements comprise the vitamins E, A and C (ascorbic acid), and one or more forms of vitamin B6. Preferably vitamin E is applied in one unit dose of the supplement in an amount of from about 200 to about 400 I.U. (international units), particularly at about 250, 300, or 350 I.U., especially about 350 I.U. Preferably vitamin A is applied in one unit dose of the supplement in an amount of from about 1500 to about 3500 I.U., particularly about 2000, 2500, or 3000 I.U., especially about 2500 I.U. Preferably vitamin C is applied in one unit dose of the supplement in an amount of from about 500 to about 1000 mg, particularly about 650, 700, 750, 800, or 900 mg, especially about 750 mg. Preferably vitamin B6 is applied in one unit dose of the supplement in an amount of from about 150 to about 750 mg (even more preferably an amount of from about 150 to about 500 mg), particularly about 200, 250, 300 or 400 mg, especially about 250 mg. Preferably pyridoxal-5'-phosphate is applied in one unit dose of the supplement in an amount of from about 25 to about 125 mg (even more preferably from about 25 to about 75 mg), particularly about 30, 35, 40, or 50 mg, especially about 35 mg.

Vitamin B6 optionally can be employed as a hydrochloride salt (e.g., supplied as vitamin B6 in the form of pyridoxine or pyridoxine hydrochloride). The coenzyme form of vitamin B6 preferably is employed as a 5'phosphate of pyridoxal. All-rac alpha-tocopherol and RRR-alpha-tocopherol and their esters are preferred as a source for vitamin E. Other sources of vitamin E include: dl-alpha tocopherol (all-rac), dl-alpha-tocopherol (RRR) and d-alpha-tocopherol and their esters such as acetate and the acid succinate; beta-tocopherol and gamma-tocopherol, and their esters; tocopheryl nicotinate, and the like. Synthetic palmitate-free Vitamin A is a preferred source of vitamin A. L-ascorbic acid is particularly preferred for the nutrient supplements of the invention. However, other forms of vitamin C also can be employed, for example, L-ascorbic acid, D-ascorbic acid, DL-ascorbic acid, D-araboascorbic acid, dehydroascorbic acids, salts of ascorbic acid, and esters of ascorbic acid. In particular, vitamin C can be employed in the form of magnesium ascorbate.

The nutrient supplements also preferably comprise taurine (a non-essential amino acid). Preferably taurine is applied in one unit dose of the supplement in an amount of from about 50 to about 150 mg, particularly about 75, 100, or 125 mg, especially about 100 mg. Taurine preferably can be employed as a salt, as either the D- or L-amino acid, or as mixtures thereof.

The nutrient supplements further preferably comprise selenium and glutathione. Selenium preferably is applied in one unit dose of the supplement in an amount of from about 5 to about 25 micrograms, particularly about 5, 10, 15, or 20 micrograms, especially about 10 micrograms. Selenium employed in the supplements optionally can be in the form of a salt (e.g., selenium picollinate), as a complex (e.g., bound to *Lactobacillus acidophilus* or yeast protein), or as a physiologically acceptable selenoprotein (e.g., selenocysteine). Glutathione can be employed, e.g., as gamma-glutamyl cysteinylglycine. Glutathione preferably is applied in one unit dose of the Basic MTP Supplement in an amount of from about 100 to about 200 mg, particularly about 125, 150, or 175 mg, especially about 150 mg, and preferably is applied in one unit dose of the Modified MTP Supplement in an amount of from about 175 to about 350 mg, particularly about 225, 275, or 325 mg, especially about 275 mg. Furthermore, other agents equivalent to glutathione that are effective for delivering cysteine can be employed instead of, or in addition to glutathione (and/or cysteine) as a means of delivering cysteine to a person.

Preferably the mixture of amino acids is supplied in one unit dose of the Basic MTP Supplement in a total amount of from about 150 to about 250 mg total amino acids, particularly about 175, 200, or 225 mg, especially about 200 mg, and is supplied in one unit dose of the Modified MTP Supplement in a total amount of from about 100 to about 200 mg total amino acids, particularly from about 110 to about 190 mg total amino acids, most particularly about 125, 150, or 175 mg, and especially an amount of about 150 mg. Preferably the amino acids are in the supplement in the form they exist in the human body, i.e., either the D- or L-amino acid, or mixtures thereof.

Thus, preferably one unit dose of the Basic MTP Supplement comprises from about 37.5 to about 62.5 mg of cysteine (especially about 50 mg of cysteine), from about 20.5 to about 34.4 mg of serine (especially about 27.4 mg of serine), from about 26.8 to about 44.6 mg of lysine (especially about 35.7 mg of lysine), from about 12.6 to about 21.0 mg of alanine (especially about 16.8 mg of alanine), from about 8.70 to about 14.5 mg of glycine (especially about 11.6 mg of glycine), from about 6.45 to about 10.8 mg of threonine (especially about 8.6 mg of threonine), from about 5.25 to about 8.75 mg of proline (especially about 7.0 mg of proline), from about 6.38 to about 10.6 mg of aspartic acid (especially about 8.5 mg of aspartic acid), from about 4.13 to about 6.88 mg of asparagine (especially about 5.5 mg of asparagine), from about 9.00 to about 15.0 mg of glutamic acid (especially about 12.0 mg of glutamic acid), from about 4.73 to about 7.88 mg of methionine (especially about 6.3 mg of methionine), from about 3.30 to about 5.50 mg of glutamine (especially about 4.4 mg of glutamine), from about 3.00 to about 5.00 mg of isoleucine (especially about 4.0 mg of isoleucine), and from about 1.65 to about 2.75 mg of valine (especially about 2.2 mg of valine).

Preferably the Modified MTP Supplement comprises all these ingredients except for cysteine. In other words, preferably one unit dose of the Modified MTP Supplement comprises from about 20.5 to about 34.4 mg of serine (especially about 27.4 mg of serine), from about 26.8 to about 44.6 mg of lysine (especially about 35.7 mg of lysine), from about 12.6 to about 21.0 mg of alanine (especially about 16.8 mg of alanine), from about 8.70 to about 14.5 mg of glycine (especially about 11.6 mg of glycine), from about 6.45 to about 10.8 mg of threonine (especially about 8.6 mg of threonine), from about 5.25 to about 8.75 mg of proline (especially about 7.0 mg of proline), from about 6.38 to about 10.6 mg of aspartic acid (especially about 8.5 mg of aspartic acid), from about 4.13 to about 6.88 mg of asparagine (especially about 5.5 mg of asparagine), from about 9.00 to about 15.0 mg of glutamic acid (especially about 12.0 mg of glutamic acid), from about 4.73 to about 7.88 mg of methionine (especially about 6.3 mg of methionine), from about 3.30 to about 5.50 mg of glutamine (especially about 4.4 mg of glutamine), from about 3.00 to about 5.00 mg of isoleucine (especially about 4.0 mg of isoleucine), and from about 1.65 to about 2.75 mg of valine (especially about 2.2 mg of valine).

Accordingly, the present invention provides a nutrient supplement, particularly a nutrient supplement suitable for treating a patient having a predisposition to develop autism or a patient having autism, wherein the supplement comprises zinc, vitamin B6, pyridoxal-5'-phosphate, vitamin E, vitamin A, vitamin C, selenium, glutathione, and taurine in amounts effective for such treatment. The nutrient supplement further preferably comprises a mixture of amino acids effective for promoting metallothioneins in a person, particularly the amino acids serine, lysine, alanine, glycine, threonine, proline, aspartic acid, asparagine, glutamic acid, methionine, glutamine, isoleucine, and valine, and also optionally cysteine.

Preferably, preservatives also can be added to the nutrient supplements (e.g., prepared liquid formulations) according to the invention. Any suitable preservative can be employed, so long as the preservative does not negate other desirable properties of the nutrient supplements, or have undesirable side effects in persons (i.e., in autistic persons as compared with non-autistic persons). Preferred preservatives include, but are not limited to, sodium benzoate and potassium sorbate which can be obtained from any commercial supplier. Preferably these preservatives are of a high purity grade. For example, these preservatives can be obtained from Spectrum Quality Products, Inc. (Gardena, Calif., Catalog Numbers S1146 and P1408, respectively), or from Sigma-Aldrich (St. Louis, Mo., Catalog Numbers B3420 and S7420, respectively). Other appropriate preservatives are alcohol (from about 15 to about 20%), benzoic acid (about 0.1%), methylparaben (from about 0.025% to about 0.2%), propylparaben (from about 0.025% to about 0.2%), and sorbic acid (about 0.1%). Sodium benzoate and potassium sorbate (or other appropriate preservatives) also can be employed in the liquid formulations of the invention in amounts ranging from about 0.01% to about 1.0% by weight (mass/volume, such as g/l) of the liquid formulations, even more preferably from about 0.05% to about 0.5% by weight (mass/volume), and especially from about 0.1% by weight (mass/volume).

Optionally, sweeteners can be added to the nutrient supplements of the invention, for instance, to make the powder or liquid formulations more palatable, e.g., sweeteners such as natural sugars (e.g., glucose, sucrose, fructose) and synthetic sugars (e.g., saccharin, cyclamates, Aspartame, etc.). Care must be taken with use of natural fructose sweeteners, however, since a high fructose content has been suggested to exacerbate copper deficiency and to be associated with heart disease characterized by high triglyceride levels. Other preferred natural sweeteners that can be employed in the invention, include but are not limited to: Bee Honey (Dutch Gold Honey, Lancaster, Pa.); Organic Bee Honey (miscellaneous vendors); Barley Malt syrups (Briess Industries New York, N.Y.); deionized fruit juice (Daystar-Robinson, Lake Success, N.Y.); Fruitrim liquid (Adept Solutions); Brown rice syrups (California Natural Products Santa Barbara, Calif.); Organic brown rice syrup (California Natural Products); Oat syrup (T & A Gourmet); Raw or Turbinado sugar (C & H sugar La Palma, Calif.); Sucanat (Wholesome Foods Palm Bay, Fla.); Organic Sucanat (Wholesome Foods Palm Bay, Fla.); Organic Sugar (Wholesome Foods Palm Bay, Fla.); Evaporated cane juice (Florida Crystals Palm Beach, Fla.); and Ki-Sweet (kiwi fruit sweetener, marketed on the Internet), as well as other sweeteners. The amount of sweetener effective in the supplement depends on the particular sweetener used and the sweetness intensity desired, and can range from about 0.1% to about 70%.

Also, with nutrient supplements formulated as powders, capsules, or tablets (i.e., solid nutrient supplements), other carbohydrates customary in tablets and powders can be employed, e.g., starches, modified starches, maltodextrins, and the like.

Flavoring agents also optionally can be added to the nutrient supplements of the invention, for instance, to make the liquid formulations more palatable. The flavor employed in the invention can be any flavor, e.g., cranberry, grape, orange, raspberry, banana, lime, lemon, cherry, grapefruit, apple, peach, tea, cola, as well as any other flavor, but preferably, is a palatable flavor which does not negate the beneficial effects of the liquid formulations, or have untoward effects in autistic patients (as compared with non-autistic patients). The amount of flavor added can vary with the flavor(s) employed, the flavor impression desired, the form of the supplement, and the form of the flavor component. However, preferably the flavor comprises from about 2.0% to about 4.0% (volume/volume) of the liquid formulations of the invention, even more preferably from about 3.0% to about 3.5% (volume/volume), and especially about 3.25% (volume/volume).

The nutrient supplements of the invention preferably can contain other natural and man-made compounds such as would be appropriate for a particular application, e.g., other carriers, stabilizers, preservatives, active agents, etc., so long as these other compounds do not negate the desirable properties of the nutrient supplements. In particular, tablets optionally may contain suitable binders, lubricants, diluents, disintegrating agents, coloring agents, flow-inducing agents, melting agents, and the like. Liquid formulations optionally may contain suitable solvents, emulsifying agents, suspending agents, diluents, melting agents, coloring agents, and the like. Of course, any component that detracts from or negates the desirable benefits of other components present in the nutrient supplements, or which has negative effects in the persons being treated (e.g., autistic persons or persons predisposed to autism as compared with non-autistic persons or non-predisposed persons) should not be employed.

Methods of Preparing the Nutrient MTP Supplements

Solid nutrient MTP Supplements according to the invention preferably can be prepared by obtaining pure nutrient substances in the appropriate proportions and dry blending these substances, e.g., using a powder mill unit, until they mix to form a resultant multinutrient powder. Preferably blending is done under conditions which yield particle sizes of less than about 50 microns, although particle size can vary dependant on the final form of the nutrient supplement. Preferably, the resulting powder of a sufficient amount than can be packed in capsule shells, e.g., such as the opaque nonallergenic capsule shells having an outer dimension length of 18 mm and a 6 mm diameter which are supplied by Parke Davis Company, or can be pelleted into tablets (e.g., by compressing the final blend on a suitable rotary tablet press equipped with capsule shape tooling). Alternately, the powder preferably can be used "as is" (i.e., sprinkled onto foods), or mixed with water or other liquid to form a liquid nutrient supplement. Most preferably, however, liquid nutrient supplement formulations are prepared by adding water (or other liquid) to solid ingredients with agitation in a suitable mixer. Optionally, with addition of vegetable oil, and transfer and agitation of the mixture in a suitable rotary die soft gelatin encapsulator, an easily swallowed soft gelatin capsule can be obtained.

Furthermore, the present invention also contemplates that independent components of a MTP Supplement can be administered independently, either at different times, or concurrently, but in a separate formulation. This particularly is true during the early phases of treatment (i.e., Phase 1, and the early part of Phase 2), as described below, in which administration is gradually increased to achieve administration of the full recommended doses of the independent components. During these early phases, it may be desirable to administer certain nutrients or components as either an "a.m." and/or "p.m." dose, or as a midday dose.

Metallothionein Promotion

This invention concerns the use of nutrient supplements which appear to act by promoting the in vivo concentration and/or activity of metallothioneins (i.e., "metallothionein promotion" or "promoting metallothioneins"). The manner in which MTs or MT functioning is regulated (i.e., and thus the manner in which "promotion" can be effected) currently is a matter of intense research.

However, the expression of a specific gene such as an MT gene can be regulated at any step in the process of producing an active protein, and can be regulated at more than one level. For instance, modulation of total protein activity can occur at least via transcriptional, transcript-processing, translational and post-translational mechanisms. Transcription can be modulated by altering the rate of transcriptional initiation or the progression of RNA polymerase (e.g., in a temporal and/or time-specific manner). Transcript-processing can be influenced by circumstances such as the pattern of RNA splicing, the rate of mRNA transport to the cytoplasm, capping, polyadenylation, and mRNA stability. These processes impact the amount of mRNA and consequently, the amount of protein, produced. Translation can be modulated, among other things, by control of how often an mRNA is translated. Post-translational mechanisms include modifications such as glycosylation, processing such as cleavage, control of protein stability, and reversible changes such as phosphorylation or reaction to allosteric effectors (e.g., feedback inhibition). These processes impact the amount of protein, and the amount of active protein, available.

It is known that chemicals, both organic (e.g., glucocorticoids) and inorganic (e.g., metal ions) can non-specifically modulate transcription of MT genes. Mammalian MT genes are transcriptionally activated by metals such as Cd and Zn through multiple copies of the metal responsive element (MRE) present in the 5'-flanking region. There also may be evidence of post-transcriptional regulation of MTs (McCormick et al., J. Biochem., 273, 185-188 (1991)).

Accordingly, metallothionein promotion according to the invention can be accomplished at either the transcriptional, post-transcriptional, translational, functional, or other level.

Effective Amount(s)

Administration of the nutrient MTP Supplement of the invention calls for administration of an "effective amount" or "sufficient amount" of the nutrient supplements (or components thereof). Such administration of the invention shall mean administration of the amount each nutrient (e.g., as present in the MTP Supplement) that is required to bring about the desired nutritional, behavioral, and/or therapeutic response. The formulations described herein provide generic means of treatment, although introduction of such treatment, and further optimization of such treatment (if necessary or desired) may vary considerably according to the individual, his or her genetic makeup, age, size, weight and environment. In some instances, and particularly in optimization of a response, it is difficult to categorically state that "x" grams, milligrams, micrograms, etc. of any given nutrient is sufficient/optimal and this may have to be empirically determined. It is within the skill in the art to modify the treatment (should this be necessary or desired) for each individual. Despite this fact, it is at least possible to assess the effectiveness of treatment with the MTP Supplements (or components thereof) by making use of various "end points" of treatment. These would be obvious to one of skill from the disclosure provided herein For instance, the effective amount preferably is that which upon administration results in: (1) a reduction of a patient's reported symptoms; (2) an increase in the amount or activity of metallothioneins (e.g., of one or more metallothioneins); (3) detoxification by removal of excess heavy metals; (4) normalization of metal metabolism; and (5) results and other therapeutic changes that can be empirically assessed.

A reduction of a patient's reported symptoms can be an important measure in the treatment of certain diseases, disorders, and conditions. For instance, pain is a subjective symptom which signifies an underlying problem. A report of pain reduction following administration of the MTP Supplements thus can be employed as a measure of effectiveness in treating an underlying problem. Any other such subjective measure (even one that can, in some fashion, be measured objectively) similarly can be employed. For instance, confusion, nervousness, irritability, can be employed, as well as any other "symptom" that a patient might report.

Metallothionein promotion (e.g., an increase in the amount or activity of one or more metallothioneins) can be assessed by monitoring the levels and/or activity of metallothioneins in a person. For instance, monitoring of levels can be done by isolating MTs, and their activity further optionally can be characterized following such isolation.

An "isolated" MT is an MT that is found in a condition other than its native environment, such as apart from blood, urine, tissue, and the like. In a preferred form, the isolated MT is substantially free of other MT isoforms. Preferably the isolated MT is free of associated metals. In order to quantify an MT or particular MT isoform, however, it is not strictly necessary to isolate the MT. (See, e.g., Chassaigne et al., Anal. Chem., 1998, 70, 2536-2543; Chassaigne et al., J. Anal. Chem., 1999, 363, 522-525; Chassaigne et al., J. Chromatogr., 1998, 828, 127-136).

A variety of techniques can be used for isolation and/or quantification and/or further characterization of metallothioneins, e.g., to assess MT promotion. For instance, chromatographic separation techniques such as HPLC and GF. This optionally can be followed by characterization of metal complexes with UV, IR, EPR. Moreover, different isoforms of metallothioneins can be isolated and purified, e.g., by applying to Sephadex G-25 or another appropriate column to gain the MTs free of metals, and then optionally using circular dichroism (CD) spectroscopy and ultraviolet (UV) absorption spectrophotometry, for instance, to assess the competition reaction and replacement reaction of MTs as part of their characterization. Metallothioneins also can be characterized by their molecular weight, heavy metals bound to the protein, and by the composition of amino acids, to name but a few.

Furthermore, analytical methods for isolating and quantifying metallothioneins by means of GFC, IEC and RP-HPLC are available and/or can be further developed or adapted. For instance, with use of an RP-HPLC method, it is possible to separate the metallothionein isoforms (See, e.g., Studer et al, J. Liq. Chrom. & Rel. Technol., 20(4), 617-625 (1997), Studer et al., Biochem. J., 328, 63-67 (1997)). Immunohistochemical means of isolating and quantifying metallothioneins also are known in the art (e.g., Zambenedetti et al, Journal of Chemical Neuroanatomy, 15, 21-60 (1998), as are MT-specific antibody and flow cytometry (Yurkow et al., J. Toxicol. Environ. Health, 54(6), 445-57 (1998)).

Other references also describe the isolation, quantitation and/or characterization of MTs. In particular, Stillmore et al. (Eds.) describes metallothioneins generally, as well as their: isolation and purification; structural characterization; spectroscopic characterization; reactivity; preparation; isolation and detection by chromatography; HPLC-atomic absorption spectrometry; HPLC-inductively coupled plasma atomic emission spectrometry; crystal structure; optical spectroscopy; absorption spectral features; circular dichroism spectral features; magnetic circular dichroism spectral intensity; emission spectral features; kinetic reactivity; formation of metal-thiolate clusters; metal-exchange reactions; ligand substitution reactions; and sulfhydryl reactivity, to name but a few (See, Stillmore et al. (Eds.), "Metallothioneins: Synthesis, Structure and Properties of Metallothioneins, Phytochelatins and Metal-Thiolate Complexes" (1992)). (See also: Vasak, Metallobiochemistry, 205, 39-41(1991); Vasak, Metallobiochemistry, 205, 41-44 (1991); Vasak, Metallobiochemistry, 205, 44-47 (1991); Robbins et al., Metallobiochemistry, 205, 485-502 (1991); Wuthrich, Metallobiochemistry, 205, 502-520 (1991); Vasak, Metallobiochemistry, 205, 520-528 (1991), and well as others).

Accordingly, it is known in the art how to quantitate and/or isolate MTs, or a specific MT isoform. Any appropriate technique can be employed in the context of the invention to assess MT promotion.

The effectiveness of MTP Supplement therapy (or treatment with components of the MTP Supplement) also can be assessed by measuring detoxification, i.e., removal of excess heavy metals. Typically such a measure is made during the early phases of treatment, as discussed below. "Normal" or standard values for levels of heavy metals (e.g., copper, zinc, cadmium, etc.) are known, as are any of a variety of tests for measuring such levels, e.g., urine, blood, hair, stool, as well as other tests. Any of these tests which is appropriate can be employed according to the invention to assess the effectiveness of treatment.

The effectiveness of MTP Supplement therapy (or treatment with components of the MTP Supplement) also can be assessed by measuring normalization of metal metabolism, i.e., the maintenance of an absence of excess heavy metals from the system. Typically such a measure is made during the later phases of treatment, as discussed below. Measures of normalization can be made as for measures of detoxification. For detoxification, however, any reduction in an amount of an excess heavy metal can be considered to signal the efficacy of the treatment, even though a "normal" value might not be obtained. By comparison, for normalization, preferably an approximately "normal" value for a heavy metal (or as normal as possible value for the individual) is obtained. Moreover, normalization also preferably can entail ensuring that certain ratios of levels fall within a certain range (e.g., the ratio of the copper and zinc levels).

Thus, preferably, the amount effective for detoxification is one that results in any reduction in any level (i.e., at least one level) of a heavy metal (i.e., a heavy metal that is in excess). Also, preferably, the amount effective for normalization is one that results in a change in a level of at least one heavy metal to fall within the normal range.

Other end points of treatment that can be employed to assess the effectiveness of the treatment using the MTP Supplement include results and other therapeutic changes that can be empirically assessed. These include measures such as social interaction, communication, laboratory reported values, and the like. It also is possible that the positive results obtained with use of the MTP Supplements is not due not to the MTs per se, but instead is due to an effect on other proteins or other molecules impacted by (e.g., regulated by) metallothioneins. The ordinary skilled artisan would understand how to design an assay, if desired, to assess such a secondary impact of MTs.

Generic Methods of Treatment According to the Invention

The generic methods of treatment of autism according to the invention have at least three applications: (1) for use in those individuals for whom any possibility of the development of autism is not an option (for instance, even in those cases where there is no evidence of predisposition); (2) for infants and small children known to be at risk for developing autism, and (3) for persons already diagnosed with autism. The major treatment difference is that many patients with autism exhibit severe digestive problems which could complicate treatment. If digestive problems exist, then the treatment herein with the MTP Supplement further may include treatment for malabsorption, or a special diet (e.g., a casein-free and/or gluten-free diet). The products of the invention, or other similar-type products can be employed in an autism treatment regimen on the basis that desirably they alleviate symptoms of and/or correct inborn error(s) of metal metabolism.

A "treatment regimen" as used herein means any program employed for promoting autism alleviation, or for preventing or delaying the onset of autism, or for treatment of any other disease, disorder, or condition, that involves administration of the nutrient supplements (e.g., an MTP Supplement such as the Basic MTP Supplement or the Modified MTP Supplement), or components of these supplements (e.g., as in Phase 1 or Phase 2 of treatment) as described herein. A "program" means that a course of action (e.g., consumption of a nutrient supplement composition according to the invention) is repeated for a period of time, e.g., desirably minimally for a period of from about one week to preferably, throughout most or all of an individual's lifetime. When employed to prevent or delay the onset of autism, to promote the reduction of the symptoms of autism, or in the treatment of any other disease, disorder, or condition, it is preferable that the nutrient supplement is consumed on at least a daily basis (as further described below) for a period of time preferably ranging from about one week to preferably, throughout most or all of a person's lifetime. The use of any nutrient supplement as described herein (and particularly the use of an MTP Supplement such as the Basic MTP Supplement or the Modified MTP Supplement) preferably is done under the guidance of a physician, and furthermore, preferably is administered in gradually increasing doses until the full dose is achieved.

All treatment programs and particularly the autism treatment programs preferably involve a two-phase treatment modality to reflect the reality that many autistic patients or individuals predisposed to autism already have a toxic heavy-metal overload when treatment begins (i.e., due to the metal metabolism disorder), and possess inadequate zinc levels. Thus, desirably treatment entails a "Phase 1" of treatment where the persons are detoxified by removal of heavy metals (e.g., copper and toxic metals) and zinc levels are built up (if necessary), and preferably this is followed by a "Phase 2" of treatment where metal metabolism is normalized and metallothioneins are promoted. However, a Phase 2 of treatment can be employed alone if a person already is on therapy containing zinc in an amount equivalent to the appropriate unit dosage of zinc in the MTP Supplement per recommended body weight (e.g., a person already receives from about 50 to about 150 mg/day of zinc, especially about 75 mg/day of zinc, in the case where that person would receive one unit dose/day of the MTP Supplement) or if a patient has approximately normal zinc levels (e.g., zinc levels in blood of about 90-150 micrograms/deciliter).

Detoxification by removal of the heavy metals (i.e., Phase 1) means causing the excess toxic metals to leave the body, such that the toxic metals are as close to normal (or acceptable) levels as is possible to achieve during this phase of treatment. Since the excess heavy metals typically are present at the consequence of zinc, and result in lower than normal zinc levels, detoxification also typically requires treatment of the patient with zinc ("zinc loading") to build up the patient's zinc levels. Other components of the nutrient supplement also optionally can be introduced doing Phase 1. However, in some cases of high levels of toxic metals in the body, it may be necessary or desirable to use clatherating agents (e.g., tetrathiomolybdate) and/or chelating agents (e.g., trientine, DMSA, DMSO, etc.), or other agents such as are known in the art to carry out detoxification.

Normalization of metal metabolism (i.e., Phase 2) means causing the metallothionein protein system to achieve proper functioning, e.g. such that the levels of trace metals in the body come within a normal range (and proportionately normal range vis-à-vis the ranges of levels of other trace metals), or using another appropriate measure of the functioning of the metallothionein protein system. This latter step is an important one in that it results in (1) protection from future toxic exposures, and (2) proper homeostasis of trace metals, particularly Cu and Zn. There are a number of available tests to ensure patients are detoxified by removal of heavy metals, and that metal metabolism is normalized. These include blood, hair, and urine tests for metals such as Pb, As, Cd, and the like, and are well known to those skilled in the art.

Phase 1 treatment thus desirably involves the gradual administration of zinc to build up to the amount present in the unit dosage of the MTP Supplement recommended for that person. For instance, in the case of a person that preferably would receive one unit dose/day of the MTP Supplement, desirably administration is carried out in gradually increasing amounts until a dose of about 5 mg/day of zinc (e.g., from about 50 to about 150 mg/day of zinc) is obtained. Preferably such administration of increasing amounts of zinc is carried out over from about two to about six weeks. During this time, the zinc can be introduced along with the introduction of the following nutrients in absorbable chemical form: vitamin B6, pyridoxal-5'-phosphate, ascorbic acid, vitamin E, and vitamin A. As for zinc, these additional nutrients can be given in Phase 1 according to the recommended unit dosage for the MTP Supplement. Once the full dosage of the nutrient supplement has been achieved, the full dosage preferably is maintained for about three to four weeks. It is anticipated that zinc loading and initial detoxification preferably are completed during that last three to four weeks at the full dose. Accordingly, Phase 1 of treatment (if required) typically is completed in a total of from about 2 to about 10 weeks. The reason the introduction of nutrients is "gradual" is because the metal metabolism dysfunction results in an early failure to properly process toxic metals, resulting in accumulation (or overload) of the toxic metals. This removal must be done gradually to avoid high blood pressure and other undesirable symptoms. Thus, the patient status should be closely monitored during the initial stages of treatment. In particular, appropriate testing of metal levels (e.g., particularly Zn) should be performed.

Phase 2 treatment desirably involves the gradual introduction of the full dose of the MTP Supplement (i.e., the MTP Basic Formulation or the Modified MTP Supplement) including all recommended nutrients over a period of from about 2 to about 6 weeks, as tolerated by the person, until ingestion of the full recommended amount of the complete MTP Supplement is obtained. Phase 2 treatment continues (e.g., indefinitely, or as long as necessary or desirable) after gradual build up to the full dosage has been completed. Thereafter appropriate testing of metal levels (e.g., Cu, Zn, and ceruloplasmin tests) should be performed, for instance after about 3 to 6 months, to enable the fine-tuning (if necessary or desirable) of dosage of the nutrient supplement. Furthermore, lab testing should be done on at least an annual basis, e.g., to compensate for any growth of the patient.

Accordingly, the present invention provides a method for preventing or delaying (e.g., by days, months, or years) the onset of autism in a person, wherein the method preferably comprises one or more of the following:

(a) optionally, identifying a person having a predisposition to develop autism (e.g., using the methods described herein);

(b) optionally, treating the person with a treatment regimen comprising detoxification by removal of excess heavy metals; and (c) optionally, treating the person with a treatment regimen comprising normalization of metal metabolism, such that the onset of autism in the person is prevented or delayed.

Preferably detoxification is done by administering to the person a nutrient supplement comprising zinc, vitamin B6, pyridoxal-5'-phosphate, vitamin E, vitamin A, and vitamin C (e.g., with a per unit dose as previously described). Desirably metal metabolism is normalized (e.g., metallothioneins are promoted) by administering to the person a nutrient supplement comprising zinc, vitamin B6, pyridoxal-5'-phosphate, vitamin E, vitamin A, vitamin C, selenium, glutathione, taurine, and a mixture of amino acids effective for promoting metallothioneins in the person, especially the amino acids serine, lysine, alanine, glycine, threonine, proline, aspartic acid, asparagine, glutamic acid, methionine, glutamine, isoleucine, and valine, and optionally, the amino acid cysteine. In particular, preferably normalization comprises administration (once the full dose is achieved) of the MTP Supplement (e.g., either the Basic MTP Supplement or the Modified MTP Supplement), and detoxification comprises administration of select components of the MTP Supplement (e.g., either the Basic MTP Supplement or the Modified MTP Supplement), as previously described.

The present invention also provides a method for treating a person exhibiting one or more symptoms of autism, wherein the method preferably comprises one or more of the following:

(a) optionally, identifying a patient having autism (e.g., using the methods previously described);

(b) optionally, treating the person with a treatment regimen comprising detoxification by removal of excess heavy metals; and (c) optionally, treating the person with a treatment regimen comprising normalization of metal metabolism, such that one or more symptoms of autism are improved (i.e., there is any reduction in symptom number and/or severity) in the person. Preferably detoxification and normalization are done using the nutrient supplements (and components of the nutrient supplements) as previously described.

Also as previously described, it is preferable according to the invention that administration be done such that there is a gradual build-up of nutrient doses to avoid sudden release of toxic elements (i.e., particularly toxic metals) into the bloodstream and initial worsening of symptoms. Also, a delayed response to treatment is predicted for persons with malabsorption or Type A blood. Typically, progress begins (or should begin) during the third week of treatment and plateaus after about 2-3 months of good compliance. Of course, "progress" may be determined clinically (i.e., by correction of aberrant biochemical tests or levels), by alleviation of any symptoms, such as behavioral symptoms, as well as by patients' own reports. At this point in time, there may be modification to the testing and treatment (i.e., fine-tuning of the treatment based on the initial patient response). Thus, preferably Phase 1 of treatment is concluded at most at anywhere from about three to about 12 months of treatment. This is based on laboratory tests to confirm that the patient is detoxified. Preferably Phase 2 of treatment carried out to delay the onset of autism can continue through the age of 3 years, after which time autism becomes extremely unlikely. However, Phase 2 of treatment (as well as Phase 1) also preferably can be applied when the patient is older than an age of three years, e.g., as where an older autistic child or adult is treated, or where a disease, disorder, or condition other than autism is being treated.

Preferably, the gastrointestinal tract problems that often accompany autism (e.g., inflammation of the epithelial layer of the intestines resulting from zinc deficiency or other causes) may be aggravated or caused by the MT dysfunction and may be more effectively managed, if not entirely alleviated, by treatment of the underlying cause. The most likely explanation based on the results described herein is that an inborn MT problem causes zinc depletion and a compromised gastrointestinal tract. Exposure to Hg or another divalent metal toxic dramatically worsens the situation. In addition to this, zinc deficiency typically is associated with poor immune function.

Accordingly, among other things, the present invention provides a method of using the nutrient supplement compositions according to the invention (e.g., the MTP Supplements including the Basic MTP Supplement and the Modified MTP Supplement) in a person's autism treatment or prevention program. Many of the ingredients of the nutrient supplements are already approved for human consumption and sold in various stores (e.g., in tablet form). Thus, there is a large source of data already available that supports the safety and efficacy for this use of the nutrient supplements.

Autism

The term "autism" as used herein includes those disorders autism (i.e., classical autism and autism spectrum), and pervasive developmental disorder (PDD) (i.e., with autistic tendencies) as identified by the criteria set forth in the American Psychiatric Association's Diagnostic and Statistic Manual (DSM IV, or a later version of DSM). Pervasive Developmental Disorders (as described in DSM IV) are characterized by severe and pervasive impairment in several areas of development: reciprocal social interaction skills, communication skills, or the presence of stereotyped behavior, interests, and activities. The qualitative impairments that define these conditions are distinctly deviant relative to the individual's developmental level or mental age. Pervasive Developmental Disorders include Autistic Disorder, Rett's Disorder, Childhood Disintegrative Disorder, Asperger's Disorder, and Pervasive Developmental Disorder Not Otherwise Specified. These disorders are usually evident in the first years of life and are often associated with some degree of mental retardation. Furthermore, although terms like 'psychosis' and 'childhood schizophrenia' were once used to refer to individuals with these conditions, there is considerable evidence that the Pervasive Developmental Disorders are distinct from schizophrenia.

The essential features of Autistic Disorder (described in DSM IV, Section 299.00) are the presence of markedly abnormal or impaired development in social interaction and communication and a markedly restricted repertoire of activity and interests. Manifestations of the disorder vary greatly depending on the developmental level and chronological age of the individual. Autistic Disorder is sometimes referred to as early infantile autism, childhood autism, or Kanner's autism. Early epidemiological studies suggested rates of Autistic Disorder of 2-5 cases per 10,000 individuals (with a greater frequency in males), but much higher rates have been reported recently. By definition, the onset of Autistic Disorder is prior to age 3 years.

The essential feature of Rett's Disorder (described in DSM IV, Section 299.80) is the development of multiple specific deficits following a period of normal functioning after birth. Rett's Disorder is typically associated with Severe or Profound Mental Retardation, and has been diagnosed only in females.

The essential feature of Childhood Disintegrative Disorder (described in DSM IV, Section 299.10) is a marked regression in multiple areas of functioning following a period of at least 2 years of apparently normal development. Childhood Disintegrative Disorder is usually associated with Severe Mental Retardation, and has also been termed Heller's syndrome, dementia infantilis, or disintegrative psychosis.

The essential features of Asperger's Disorder (described in DSM IV, Section 299.80) are severe and sustained impairment in social interaction and the development of restricted, repetitive patterns of behavior, interests, and activities. The disturbance must cause clinically significant impairment in social, occupational, or other important areas of functioning. In contrast to Autistic Disorder, there are no clinically significant delays in language (e.g., single words are used by age 2 years, communicative phrases are used by age 3 years). In addition, there are no clinically significant delays in cognitive development or in the development of age-appropriate self-help skills, adaptive behavior (other than in social interaction), and curiosity about the environment in childhood.

The category Pervasive Developmental Disorder Not Otherwise Specified (including Atypical Autism) (described in DSM IV, Section 299.80) is applied when there is a severe and pervasive impairment in the development of reciprocal social interaction or verbal and nonverbal communication skills, or when stereotyped behavior, interests, and activities are present, but the criteria are not met for a specific Pervasive Developmental Disorder, Schizophrenia, Schizotypal Personality Disorder, or Avoidant Personality Disorder.

Identifying a Predisposition for the Development of Autism

According to the invention, the "onset of autism" is the time at which a person begins to exhibit symptoms of autism, as described above. The methods of treatment described herein can be applied in a person who either has or has not been diagnosed as being autistic. Along these lines, the methods can be carried out in the general public to prevent or delay (i.e., by days, months, or years) the onset of autism in a person. In some instances, it might be desirable to identify those persons having a predisposition for the development of autism prior to the initiation of treatment—although such "pre-testing" is not a requirement of the invention. A "predisposition" means that the person so identified has a greater likelihood toward the development of autism at some point in time as compared with a person not having the predisposition.

Any effective and appropriate means for identifying a predisposition for the development of autism can be employed in the practice of the invention. For example, a predisposition in a person for the development of autism can be identified by such means which include, but are not limited to:

(a) collecting a person's blood;
    (b) determining the level in the person's blood of Cu; and
    (c) determining the level in the person's blood of Zn; and
    (d) calculating the ratio of Cu to Zn (i.e., in serum or in plasma), wherein a Cu/Zn ratio of greater than about 1.3 (especially a ratio of from about 1,3 to about 3.5, and ever more preferably, a ratio of greater than about 1.6) is considered to indicate a predisposition of the person to develop autism (i.e., as described in U.S. Patent Application Ser. No. 60/225,795 (now abandoned)). Preferably the ratio is calculated when Cu and Zn are measured in identical units (e.g., units of micrograms/deciliter (mcg/dl)). Moreover, the fraction of serum Cu bound as ceruloplasmin also is useful in identifying the presence of a metallothionein disorder. Namely, in healthy individuals, from about 10% to about 20% of Cu in the bloodstream is unbound by (i.e., free of) ceruloplasmin. By comparison, in untreated autistics, the percent of unbound Cu is typically between about 30% and about 60%.

Alternately, identifying a predisposition in a person for the development of autism preferably comprises:

(a) collecting the person's urine; and
    (b) determining the kryptopyrrole (Kp) level in the person's urine;

wherein a Kp level greater than about 50 mcg/dl (i.e., micrograms per deciliter) (particularly a Kp level of from about 25 to about 200 mcg/dl, and even more preferably a Kp level of greater than about 30 mcg/dl) is considered to indicate a predisposition of the person to develop autism (i.e., as described in U.S. Patent Application Ser. No. 60/225,795 (now abandoned)).

Still another preferred method of identifying a predisposition in a person for the development of autism comprises:

(a) collecting from the person a skin or blood sample; and
    (b) determining the level of metallothioneins in the person's skin or blood;

wherein a level of metallothioneins (or the level of a particular metallothionein) in the patient's skin that is significantly lower than the level of metallothioneins (or the level of a particular metallothionein) present in a significant number of children within 5 years of age of the child, and who have not developed autism, is considered to indicate a predisposition of the child to develop autism (i.e., as described in U.S. Patent Application Ser. No. 60/225,795 (now abandoned)).

Other appropriate means for identifying a predisposition in a person for the development of autism also can be employed. Such means include, but are not limited to: any appropriate genetic test (e.g., such as that disclosed in U.S. Pat. No. 6,228,582, as well as any further genetic test for autism, since, according to Dr. Eric London, Director of Medical Affairs for the National Alliance for Autism Research, geneticists "estimate as many as 15 different genes may put children at risk of developing autism" (as reported on the internet)); any appropriate enzyme, marker or substrate test (e.g., such as described in U.S. Pat. No. 5,686,311 and PCT International Application WO 01/43764); and the like. The means particularly include any appropriate test for metallothionein dysfunction, and any appropriate tests of toxic trace metals. Furthermore, exhibition of any of the symptoms of autism in the absence of exhibition of sufficient symptoms for a full diagnosis of autism (e.g., using the criteria set forth in DSM IV, or a later version of DSM) can be considered evidence of a predisposition for the development of autism.

Other Illustrative Uses of the MTP Supplements According to the Invention

In view of the apparent ability of the MTP Supplements to promote metallothioneins (and promote removal of excess metals), preferably the supplements can be employed in the treatment of any disease, disorder or condition that would benefit from such metallothionein promotion (and/or from such removal of excess metals). Recent research has indicated that Alzheimer's Disease (AD) may be caused by a metallothionein disorder. The evidence for this includes a recent finding that the MT-III concentration of AD patients is only about one third that of the normal level, and that the beta amyloid placque commonly found in AD patients results from free Cu and Zn ions attaching to normal beta amyloid. MT-III is a neuronal growth inhibitor which is involved in organization and maintenance of brain cells. Assuming AD results from an MT dysfunction, or that elements of the disease are exacerbated by an MT dysfunction, then preferably administration of the nutrient supplement formulations described herein (i.e., the Basic MTP Formulation or Modified MTP Formulation) can be advantageously employed in the treatment, prevention, and/or reversal of AD. Such treatment optimally can be employed in conjunction with recently developed tests which identify persons with a genetic tendency for AD.

As used herein, the term "Alzheimer's Disease" or "AD" refers to a progressive mental deterioration manifested by memory loss, confusion and disorientation beginning in late middle life and typically resulting in death in five to ten years. Pathologically, AD can be characterized by thickening, conglutination, and distortion of the intracellular neurofibrils, neurofibrillary tangles and senile plaques composed of granular or filamentous argentophilic masses with an amyloid core. Methods for diagnosing AD are known in the art. For example, the National Institute of Neurological and Communicative Disorders and Stroke-Alzheimer's Disease, and the Alzheimer's Disease and Related Disorders Association (NINCDS-ADRDA) criteria can be used to diagnose Alzheimer's Disease (McKhann et al., *Neurology*, 34, 939-944 (1984)). The patient's cognitive function can be assessed by the Alzheimer's Disease Assessment Scale-cognitive subscale (ADAS-cog; Rosen et al., *Am. J. Psychiatry*, 141, 1356-1364 (1984)).

The nutrient supplement formulations (i.e., The Basic MTP Formulation or Modified MTP Formulation) also optionally can be employed in treating copper overload diseases, including Wilson's Disease, postpartum depression, paranoid schizophrenia, hyperactivity (particularly Attention Deficit Hyperactivity Disorder (ADHD)), and certain types of cancer (e.g., cancers resulting from metallothionein dysfunction). Also, recent studies report that metallothionein dysfunction may be a primary cause of aging, which supports utility of the nutrient supplement formulations described herein (i.e., the Basic MTP Formulation or Modified MTP Formulation) in the prevention and/or reversal of premature aging. Furthermore, reduction of metallothioneins has been shown to promote the disease expression of familial amyotrophic lateral sclerosis (FALS), which supports that the MTP Supplements can be employed in the treatment of FALS. Thus, the present invention further preferably provides a method for treating a person exhibiting one or more symptoms of a disease, disorder, or condition selected from the group consisting of Alzheimer's Disease, Wilson's Disease, postpartum depression, schizophrenia, hyperactivity, cancer, premature aging, and familial amyotrophic lateral sclerosis, and wherein the method preferably comprises administering to the person a nutrient MTP Supplement according to the invention such that one or more symptoms of the disease, disorder, or condition are improved. Schizophrenia and ADHD preferably can be assessed using DSM IV or a later version of DSM.

Other uses of the nutrient MTP Supplements would be apparent to one skilled in the art, and are contemplated in the context of the invention.

The following examples further illustrate the present invention, but should not be construed in any way as limiting its scope.

EXAMPLE 1

The present invention provides preferred MTP Supplements containing mixtures of various amino acids, among other things, proposed for promoting metallothioneins. A variety of protein supplements presently marketed or proposed also contain amino acids. The amino composition of the MTP Supplement (i.e., the Basic MTP Formulation) was compared against these protein supplements. Two representative supplements are compared with the MTP Supplement (i.e., the Basic MTP Formulation) in Table 7.

TABLE 7

Comparison of Two Sample Protein Supplements with the MTP Supplement (i.e., the Basic MTP Formulation having preferred weight % of amino acids in the amino acid mixture)

|  | Protein Supplement 1 (LPP Conc. Protein) weight % | Protein Supplement 2 (Vital Life Amino IV) weight % | Basic MTP Supplement weight % |
|---|---|---|---|
| Cysteine | 0 | 0 | 25 |
| Serine | 5 | 5.3 | 13.7 |
| Lysine | 8 | 6.4 | 17.85 |
| Alanine | 3 | 6.2 | 8.4 |
| Glycine | 2 | 9.7 | 5.8 |
| Threonine | 4 | 4.2 | 4.3 |
| Proline | 8.5 | 3.7 | 3.5 |
| Aspartic Acid | 7 | 2.6 | 4.25 |
| Asparagine | 0 | 0.9 | 2.75 |
| Glutamic Acid | 19.5 | 7.1 | 6 |
| Methionine | 3 | 2.7 | 3.15 |
| Glutamine | 0 | 2.1 | 2.2 |
| Isoleucine | 5.5 | 6.4 | 2 |
| Valine | 6.5 | 7.4 | 1.1 |
| Leucine | 8.5 | 8.5 | 0 |
| Phenylalanine | 5 | 4.3 | 0 |
| Tryptophan | 2 | 0 | 0 |
| Arginine | 4 | 3.2 | 0 |
| Cystine | 0.5 | 6.2 | 0 |
| Histidine | 3 | 3.5 | 0 |
| Tyrosine | 5 | 6.1 | 0 |
| Taurine | 0 | 3.5 | 0 |
| Total | 100 | 100 | 100 |

Out of approximately 240 amino acid formulations examined, none were found to resemble the particular combination and amounts of amino acids employed in the MTP Supplement. The MTP Supplement (i.e., the Basic MTP Formulation) omits 8 major amino acids typically found in amino acid supplements. The amino acids leucine, phenylalanine, tryptophan, arginine, cystine, histidine, tyrosine, taurine are not present in the MTP Supplement.

EXAMPLE 2

The MTP Supplement (i.e., the Basic MTP Formulation) was administered to volunteers including certain patients of the Pfeiffer Treatment Center ("PTC", located at 1804 Centre Point Drive, Naperville, Ill. 60563). Unless otherwise noted, the MTP Supplement administered in these studies comprised amounts of each component falling within the range/unit dose set forth in Table 2, although in some instances, the supplement was not administered as a single dose/tablet, but rather was contained in more than one tablet. In most cases, following any gradual buildup to the "complete" dose, volunteers administered the dose/day specified in Table 1.

The initial tests involved eight volunteers who were known from prior testing to have a Cu/Zn imbalance, but who had no evidence of any autistic tendency, and were not receiving nutrient therapy or any other sort of therapy associated with the treatment of autism. The volunteers were all female, ranging in age from about 35 to about 55 years of age. The eight volunteers had blood levels of Zn, Cu, and ceruloplasmin taken before, and periodically after, starting on the MTP Supplement. The volunteers used the MTP Supplement in addition to their regular dietary intake, and took no vitamins during these tests. After starting on the supplement, four of the volunteers exhibited lower plasma Zn levels, along with increased irritability. Consequently, it was decided that subsequent persons receiving the supplement would receive prior to such treatment increasing amounts of zinc (i.e., up to about the amount preferred in the supplement), as well as potentially other components of the supplement, for a course of time prior to receiving the full dose of the MTP Supplement.

The next tests were done on 10 volunteers who had previously been diagnosed with and received treatment for autism, i.e., "patient volunteers". These patient volunteers had a median age median of about eight years old and approximately 80% were male All were currently receiving treatment for autism (e.g., receiving probiotic therapy, and having diets free of casein and gluten but perhaps controlled for certain other nutrients not present in the MTP Supplement) which was continued throughout these tests, but were at the time of the tests at a plateau in their treatment, and not achieving any further gains. Cautious testing of these 10 patient volunteers revealed the following: (1) four patients who had been aggressively loaded with zinc (i.e., receiving zinc levels within the range of that present in the MTP Supplement) prior to beginning the daily administration of the full dose of the MTP Supplement reported significant improvements, (2) two patients similarly loaded with zinc prior to receiving the full MTP Supplement dose reported no change, and (3) four other patients who received zinc, but not in amounts up to the level present in the MTP Supplement prior to receiving the full dose of the MTP Supplement, reported a worsening in irritability.

These findings confirmed that in most cases, loading with zinc is necessary prior to taking the MTP Supplement. The supplement appears to work best for persons who were pre-loaded with zinc for several weeks. Failure to pre-load with zinc can result in symptom worsening during initial treatment. It is possible that in the absence of such zinc loading, sudden induction of metallothionein in a zinc-depleted individual may result in additional zinc loss, since every MT molecule can bind up to seven zinc atoms. The loaded MT molecule then may exchange a zinc atom for an atom of mercury, lead, or other metal, but even so, zinc atoms can be lost as the toxic metals leave the body.

Regardless of the mechanism, subsequent to these tests, dozens of additional volunteer autistic and ADHD patients ("volunteer patients") have begun taking the MTP Supplement. Not all of the families of these volunteer patients have yet reported the results. However, such testing of the MTP Supplement to date suggests that the supplement is very powerful in altering blood levels and provoking symptom changes. Namely, lab testing has revealed generally higher levels of serum ceruloplasmin and lower levels of unbound Cu (calculated as total serum Cu minus Cu bound by ceruloplasmin), and reduced levels of excreted toxic metals (stool testing) with use of the MTP Supplement. Positive symptom changes were reported (primarily for those having had the benefit of aggressive zinc loading) including greatly improved speech, better focus and concentration, lessened irritability, reduced depression, and improved socialization. Negative symptoms (typically reported by those having had marginal zinc loading) usually involved either increased irritability or diarrhea.

Further notable and striking improvements were achieved in a number of volunteer patients (including some patients treated at the PTC) using the MTP Supplement. The following "MTP Case Histories" are exemplary of this.

MTP Case History 1:

Volunteer patient "Zachary", age 4, had been a patient of the PTC for about 16 months prior to receiving the MTP Supplement. Zachary became a patient at the Center following extensive testing resulting in a diagnosis of "Pervasive Developmental Disorder With Autistic Features". Prior to coming to PTC, Zachary's parents had been informed that Zachary (then age 2 years, 9 months) might never speak again, would likely have life-long behavioral outbursts, had an IQ of 56, and likely should be placed in an institution. The family sought treatment at PTC in an attempt to overcome this dire prognosis.

After receiving about 1 year of treatment at the PTC (including aggressive zinc therapy, metal chelation, a diet free of casein and gluten, probiotics, and nutrient programs to balance his chemistry), Zachary exhibited significant improvement. His emotional "melt-downs" had nearly ceased, he had stopped isolating from the family, and was beginning to talk. However, his metal metabolism was still aberrant (based on blood lab testing), and his speech was limited to 2-3 word sentences.

On Oct. 11, 2001, Zachary began ingesting the MTP Supplement, along with continuing on a controlled diet and probiotics. Zachary received essentially one unit dose/day, which is approximately the full recommended daily dosage for his weight per Tables 1 and 2. This was reduced after 3 days to half the unit dose/day, since the initial dose resulted in diarrhea and irritability (possibly due to too rapid of an introduction of the supplement). However, to ensure he received the appropriate balance of vitamins and zinc, additional amounts of zinc, vitamins B6, C and E, and pyridoxal-5'-phosphate were given to Zachary to bring the amounts of these components to within the range recommended in Table 2.

The family reported that over the next 7 days of this regimen, Zachary began to speak in complex sentences, and for the first time, engaged in imaginative play. He visited PTC one month after starting taking the MTP Supplement, and presented as a cheerful, happy child of 4 years, with excellent communication skills. The parents report continuing progress in expressive language. Zachary's IQ currently measures above 100. Moreover, doctors independent of PTC retested Zack recently and stated that he no longer exhibited any PDD or autistic tendencies. The examining physicians were unable to explain this diagnosis reversal. Zachary is continuing to receive the MTP Supplement.

Since the MTP Supplement was the notable component that had changed in Zachary's treatment prior to the improvements, the improvements appear to be a consequence of the MTP Supplement therapy.

MTP Case History 2:

Volunteer patient "Matthew", age 11, had been a patient of the PTC for about 7 years, and came to the PTC originally with a severe behavior disorder. PTC medical staff examined Matthew and uncovered a metal metabolism disorder and a disorder of pyrrole chemistry. For several years, Matthew exhibited good progress on the PTC therapy directed at these disorders, which included aggressive zinc therapy. Despite such treatment, in the most recent year of treatment, Matthew's behavior began to worsen, his academics declined, and he was diagnosed with depression, for which his primary care physician had prescribed Paxil.

On Oct. 18, 2001, Matthew began taking the MTP Supplement (i.e., the "full dosage" of 2 unit doses/day) in addition to his prior therapies (including dietary restrictions, and, for at least part of the time of the trial, Paxil). Within two weeks his parents reported striking improvements in behavior control and depression.

Since the MTP Supplement was the notable component that had changed in Matthew's treatment prior to the improvements, the improvements appear to be a consequence of the MTP Supplement therapy.

MTP Case History 3:

Volunteer patient "Miles", age 6, had been diagnosed with autism and had responded quite well to a variety of treatments including aggressive zinc therapy, special diets, behavioral therapy, and heavy metal chelation. However, Matthew continued to be quite distant and aloof socially, and continued to test with heavy-metal overloads. Thus, Miles' family agreed to begin treating Miles with the MTP Supplement. Miles' family gradually introduced the MTP supplement over a period of about 10 days, during which time he continued on a casein-free, gluten-free diet. He ultimately was taking one unit dose/day, which was essentially a "full dose" for Miles.

Metal levels in Miles' fecal samples were tested before and after 40 days after he began the MTP Supplement therapy. The chemical results are summarized below in Table 8:

TABLE 8

Metal Levels in Patient Fecal Samples Pre- and Post-Treatment

| Metal | PPM, Pre-Treatment | PPM, Post-Treatment | % Reduction |
|---|---|---|---|
| Mercury | 0.067 | 0.024 | 64% |
| Antimony | 0.214 | 0.141 | 34% |
| Arsenic | 0.64 | 0.31 | 52% |
| Cadmium | 0.77 | 0.50 | 35% |
| Lead | 1.46 | 0.49 | 66% |

As can be seen from Table 8, there were very significant reductions in the level of toxic heavy metals following 40 days of MTP Supplement therapy. Furthermore, Miles' family reports that he has greatly advanced in socialization and calmness over this treatment period, and for the first time, will initiate physical contact, climb into his mother's lap, and exhibit other behaviors involving physical contact. Miles is continuing therapy with the MTP Supplement.

Since the MTP Supplement was the notable component that had changed in Miles' treatment prior to the improvements, the improvements appear to be a consequence of the MTP Supplement therapy.

All of the references cited herein are hereby incorporated in their entireties by reference. In particular, U.S. Patent Application Ser. Nos. 60/225,795 and 60/250,404 are incorporated by reference in their entireties.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A method for promoting metallothioneins in a person comprising administering to said person an amount effective for promoting metallothioneins of a copper-free nutrient supplement comprising from about 50 to about 150 mg of zinc, and further comprising vitamin B6, pyridoxal-5'-phosphate, vitamin E, vitamin A, vitamin C, selenium, glutathione, taurine and a mixture of amino acids consisting essentially of cysteine, serine, lysine, alanine, glycine, threonine, proline, aspartic acid, asparagine, glutamic acid, methionine, glutamine, isoleucine, and valine.

2. The method according to claim 1, wherein said amino acids comprise:
   from about 37.5 to about 62.5 mg of cysteine,
   from about 20.5 to about 34.4 mg of serine,
   from about 26.8 to about 44.6 mg of lysine,
   from about 12.6 to about 21.0 mg of alanine,
   from about 8.70 to about 14.5 mg of glycine,
   from about 6.45 to about 10.8 mg of threonine,
   from about 5.25 to about 8.75 mg of proline,
   from about 6.38 to about 10.6 mg of aspartic acid,
   from about 4.13 to about 6.88 mg of asparagine,
   from about 9.00 to about 15.0 mg of glutamic acid,
   from about 4.73 to about 7.88 mg of methionine,
   from about 3.30 to about 5.50 mg of glutamine,
   from about 3.00 to about 5.00 mg of isoleucine, and
   from about 1.65 to about 2.75 mg of valine.

3. The method according to claim 1, wherein the copper-free nutrient supplement comprises:
   about 75 mg of zinc,
   about 250 mg of vitamin B6,
   about 35 mg of pyridoxal-5'-phosphate,
   about 350 I.U. of vitamin E,
   about 2,500 I.U. of vitamin A,
   about 750 mg of vitamin C,
   about 10 micrograms of selenium,
   about 150 mg of glutathione,
   about 100 mg of taurine,
   about 50 mg of cysteine,
   about 27.4 mg of serine,
   about 35.7 mg of lysine,
   about 16.8 mg of alanine,
   about 11.6 mg of glycine,
   about 8.6 mg of threonine,
   about 7.0 mg of proline,
   about 8.5 mg of aspartic acid,
   about 5.5 mg of asparagine,
   about 12.0 mg of glutamic acid,
   about 6.3 mg of methionine,
   about 4.4 mg of glutamine,
   about 4.0 mg of isoleucine
   and about 2.2 mg of valine.

4. The method according to claim 1, wherein the copper-free nutrient supplement comprises from about 150 to about 750 mg vitamin B6.

5. The method according to claim 1, wherein the nutrient supplement comprises from about 25 to about 125 mg of pyridoxal-5'-phosphate.

6. The method according to claim 1, wherein the nutrient supplement comprises from about 200 to about 400 I.U. of vitamin E.

7. The method according to claim 1, wherein the nutrient supplement comprises from about 1,500 to about 3,500 I.U. of vitamin A.

8. The method according to claim 1, wherein the nutrient supplement comprises from about 500 to about 1000 mg of vitamin C.

9. The method according to claim 1, wherein the nutrient supplement comprises from about 5 to about 25 micrograms of selenium.

10. The method according to claim 1, wherein the nutrient supplement comprises from about 100 to about 200 mg of glutathione.

11. The method according to claim 1, wherein the nutrient supplement comprises from about 50 to about 150 mg of taurine.

* * * * *